United States Patent [19]

Gosciniak

[11] Patent Number: 4,935,533

[45] Date of Patent: Jun. 19, 1990

[54] ULTRAVIOLET RADIATION ABSORBING COMPOSITIONS OF 1-CYCLOHEXENYLACETONITRILE DERIVATIVES OF ALDEHYDES

[75] Inventor: Donald J. Gosciniak, West Chester, Pa.

[73] Assignee: ICI Americas Inc., Wilmington, Del.

[21] Appl. No.: 290,977

[22] Filed: Dec. 28, 1988

[51] Int. Cl.$^5$ .......................... A61K 7/40; A61K 7/42; A61K 9/107; C07C 255/49

[52] U.S. Cl. ........................................ 558/388; 106/3; 106/14.34; 106/14.35; 106/400; 424/47; 424/59; 424/60; 424/63; 424/64; 514/847; 514/873; 514/938; 558/401; 558/403; 558/406; 558/408; 558/409; 558/410

[58] Field of Search ............... 558/388, 401, 403, 406, 558/409, 408, 410

[56] References Cited

U.S. PATENT DOCUMENTS 2,647,122 7/1953 Archer et al. .................. 558/388 X
2,773,857 12/1956 Pratt ............................... 558/388 X

*Primary Examiner*—Dale R. Ore
*Attorney, Agent, or Firm*—William E. Dickheiser

[57] ABSTRACT

Sunscreen compositions are described which contain certain 1-cyclohexenylacetonitrile derivatives of aldehydes which act as UV filters when incorporated in a carrier in amounts ranging from 0.1–50% by weight.

5 Claims, No Drawings

ULTRAVIOLET RADIATION ABSORBING COMPOSITIONS OF 1-CYCLOHEXENYLACETONITRILE DERIVATIVES OF ALDEHYDES

The present invention is directed to ultraviolet absorbing compositions comprising certain conjugated 1-cyclohexenylacetonitrile derivatives of aldehydes and blends thereof which are useful as protective coatings and to a method for protecting substrates against the harmful effects of actinic radiation. It is further directed to a process for making ultraviolet absorbing coating compositions.

Ultraviolet radiation absorbing coatings are useful in protecting substrates such as plastics against accelerated deterioration and the skin of warm blooded animals against severe erythema, edema and blistering when exposed to sunlight. The cyclohexenylacetonitrile compositions of this invention are generally referred to as sunscreen compositions and blends thereof can be incorporated with waxes, oils, lacquers and soft resins in the preparation of furniture and auto polishes, as well as cosmetics, suntan oils, lotions, lipstick, hair treatments, skin formulations and in addition can be incorporated with contact lenses.

This invention relates to sunscreen compositions comprising a carrier having incorporated therein an effective amount of a ultraviolet absorber selected from a compound of general Formula I:

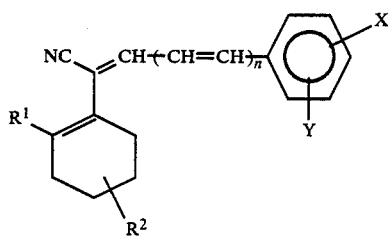

wherein n is 0 or 1, but when n is 0, $R^1$ is H, an alkyl group having from 1 to 10 carbon atoms $R^2$ is H, an alkyl group having from 1 to 10 carbon atoms, $-OR^3$, $-NHR^3$, $-N(R^3)_2$ and $-CO_2R^3$ where $R^3$ is an alkyl group having from 1 to 10 carbon atoms and X and Y are independently selected from H, alkyls of from 1 to 10 carbon atoms, halogen, $-CN$, $-NO_2$, $-NHR^4$, $-N(R^4)_2$, $-OR^4$, $-CO_2R^4$ where $R^4$ is an alkyl group having from 1 to 10 carbon atoms and when n is 1, $R^1$ and $R^2$ are as described above and X and Y are hydrogen.

The method for protecting substrates comprise topically applying the compound of formula I in an acceptable carrier. Of particular interest are compounds which provide selective absorption of UV radiation in the 290–320 nm as well as the 320–400 nm range of wave lengths. The compounds may be dissolved in the coating compositions or present as a finely divided solid or as a solid dispersed in an acceptable carrier. The selection of carrier used in the coating composition must not interfere with the absorption in the 290–400 nm range. In some instances interaction of the bis-diketone with a carrier shifts absorption outside the desired range and is not acceptable.

The compositions of the invention comprise UV filter compounds of Formula I in amounts needed to provide desired protection against the harmful effects of ultraviolet radiation. The concentration of the compounds in the composition is regulated such that when the composition is topically applied, the desired protection is provided. The amount needed to provide the desired protection can vary with the characteristics of the compound, that is, its extinction coefficient or substantively, the nature of the carrier, the source and intensity of the radiation and other well recognized variables. Suitable amounts can be readily determined by standard methods of testing. Preferably UV filter compounds are incorporated in an amount ranging from about 0.1 percent to about 50 percent by weight and usually in amounts of 1.0–30 percent by weight and preferred amounts ranging from 1.5–15 percent by weight based on the total weight of the coating composition.

Acceptable carriers include any vehicle or medium capable of incorporating the UV filter compound in a manner permitting uniform topical application. The term "pharmaceutically acceptable" is intended as a qualifier when the carrier is dermatologically innocuous to warm blooded animals and cosmetically acceptable. However all carriers are not useful on skin. The carrier may comprise a wax, oil or cream base material in which the agent can be held in a clear solution or a uniform dispersion for example as submicron sized particles. Preferably the carrier comprises a suitable solvent or a mixture of solvents capable of dissolving the UV filter compounds to provide a concentration that is effective as a filtering agent when incorporated in the sunscreen formulation. Solvents which may be useful include alcohols, ketones, esters, polyol esters, oils, hydrocarbons, chlorinated hydrocarbons, ethers, polyethers, polyether polyols and other special solvents such as dimethylsulfoxide, dimethylformamide, dimethylisosorbide, isopropylmyristate and the like. Such solvents are considered useful only if they do not permanently interact with the active UV filtering compound of the invention to shift the total effective absorption outside the 290–400 nm range. Some of the above named ingredients are not pharmaceutically acceptable but are useful in other applications.

The invention is directed to a method for protecting a substrate against the effects of ultraviolet radiation which comprises topically applying the above described compounds in a carrier.

The sunscreening compositions may be applied as a clear liquid or a lotion comprising a water-in-oil, oil-in-water or a multiple emulsion. Either the oil or water base or both may be used as a carrier for the sunscreening composition. The oil base material and the water and oil base compositions will form a continuous film of the UV filtering compound. Such films also provide long lasting protection against sun induced erythema. Sunscreening formulations are generally used in hot weather and at beaches where people enjoy bathing activity. It is also essential that the protective coating applied to the skin is not appreciably affected by water or perspiration. The pharmaceutically acceptable compositions herein disclosed are included in a thin layer protective coating on the skin of warm blooded animals and provide long lasting protection against erythema and do not appreciable decompose over practical periods of exposure to sunlight.

In general the compounds are synthesized by reaction of the anion of 1-cyclohexenylacetonitrile with an aldehyde such as benzaldehyde or cinnamaldehyde in an alcoholic solvent such as ethanol or methanol.

The following compounds exemplify, but do not limit, the active compounds of the Formula I:

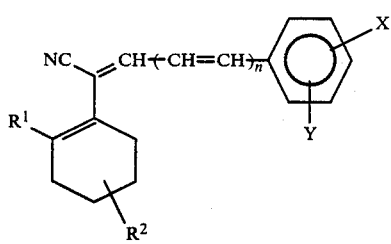

2-(1-cyclohexenyl)-5-phenyl-2,4-pentadienenitrile 2-(4-t-butyl(1-cyclohexenyl))-5-phenyl-2,4-pentadienenitrile
2-(1-cyclohexenyl)-3-phenyl-2-propenenitrile 2-(1-cyclohexenyl)-3-(4-methoxyphenyl)-2-propenenitrile
2-(1-methyl-4-t-butyl(1-cyclohexenyl))-5-phenyl-2,4-pentadienenitrile
2-(1-cyclohexenyl)-3-(2,5-dimethoxyphenyl)-2-propenenitrile
2-(1-cyclohexenyl)-3-(3-methyl-4-methoxyphenyl)-2-propenenitrile
2-(1-cyclohexenyl)-3-(4-t-butylphenyl)-2-propenenitrile
2-(1-cyclohexenyl)-3-(2,4-dimethylphenyl)-2-propenenitrile
2-(1-cyclohexenyl)-3-(4-dimethylaminophenyl)-2-propenenitrile
2-(1-cyclohexenyl)-3-(4-carboethoxyphenyl)-2-propenenitrile
2-(4-t-butyl(1-cyclohexenyl))-3-phenyl-2-propenenitrile Compounds wherein n is 0 can be prepared by reacting an appropriately substituted benzaldehyde with 1-cyclohexenylacetonitrile in an alcoholic sodium hydroxide solution. Other bases such as alkoxides, carbonates, sodamide, sodium hydride and alkyl lithiums to name a few are also effective in these reactions. The substituted benzaldehydes are either commercially available or can be synthesized by established preparative procedures. 1-Cyclohexenylacetonitrile and derivatives can be conveniently prepared by the method of A. C. Cope et. al. (Org. Synth. 31, 25 (1951). Compounds wherein n is 1 are prepared similarly by substituting a properly functionalized cinnamaldehyde for the benzaldehyde derivative. The cinnamaldehyde compounds not commercially available can be conveniently prepared by the method of Wittig et. al. (U.S. #3,365,481).

The following preparative examples serve as nonlimiting illustrations of the type of compounds included in the invention and all parts and percentages are expressed on a weight basis unless otherwise specified.

PREPARATION 1

Synthesis of
2-(1-cyclohexenyl)-5-phenyl-2,4-pentadienenitrile

In a 50 ml 3-necked round bottom flask equipped with a nitrogen inlet, condensor and magnetic stir bar is placed cinnamaldehyde (2.64 g, 0.02 mol), 1-cyclohexenylacetonitrile (2.42 g, 0.02 mol) and sodium hydroxide (0.2 g, 0.005 mol) in absolute ethanol (25 ml). The reaction is stirred at room temperature until completion, during which time the crude product precipitates from solution. The precipitate is filtered, washed with water and dried. Recrystallization from ethanol yields a yellowish solid with maximum absorption at 338 nm and extinction coefficient of 45,825.

PREPARATION 2

Synthesis of
2-(4-t-butyl(1-cyclohexenyl))-5-phenyl-2,4-pentadienenitrile

The procedure of Preparation 1 was followed using 1-(4-t-butyl) cyclohexenylacetonitrile (3.43 g, 0.02 mol) in place of 1-cyclohexenylacetonitrile. Recrystallization from ethanol yielded a yellowish solid with a maximum absorption at 336 nm and extinction coefficient of 44,523.

PREPARATION 3

Synthesis of
2-(1-cyclohexenyl)-3-phenyl-2-propenenitrile

The procedure of preparation 1 was followed using benzaldehyde (22.12 g, 0.02 mol) in place of cinnamaldehyde. Recrystallization from ethanol afforded a white solid with maximum absorption at 304 nm and an extinction coefficient of 23,617.

PREPARATION 4

Synthesis of
2-(1-cyclohexenyl)-3-(4-methoxyphenyl)-2-propenenitrile

The procedure of Preparation 1 was followed using anisaldehyde (2.72 g, 0.02 mol) in place of cinnamaldehyde. Recrystallization from ethanol afforded a white solid with maximum absorption at 327 nm and extinction coefficient of 26,768.

It has been established that actinic radiation between 290 nm and 320 nm produces substantially all the burning or erythemal energy and a substantial portion of the tanning energy, while the radiation between 320 nm and 400 nm produces incident tanning. The cosmetic industry has divided these spectra into the burning range UV-B, (290–320 nm) and the tanning range UV-A (320–400 nm). Since approximately 76% of the physiological tanning potential of sunlight is found in the UV-B range and the balance is found in the UV-a range, it is desirable to have a substantial amount of the radiation in those ranges filtered out before it produces a harmful effect on the surface of human skin. While sunscreen lotions have been formulated to be most effective in the UV-B range recent studies have indicated that it is desirable to have collective adsorption in the UV-A range as well. It has been difficult to find a practical compound which effectively absorbs in both ranges. Therefore, formulators must resort to the combination of two compounds which are each effective either in the UV-B, or UV-a range to provide maximum skin protection. No single compound falling within the definition of formula I is effective over the entire 290–400 nm range and therefore two or more compounds can be selected and blended within the formulation at varying concentrations until the desired balance between burning and tanning is accommodated. Such a combination is shown in Example 13. It is preferred to have a formulation having at least one compound which absorbs in the 290–320 nm range and at least one other which absorbs in the 290–320 nm range and at least one other which absorbs in the 320–400 nm range. At least one is selected from Formula I.

The use of the UV filters of the invention can be demonstrated in lotion formulations which are topically applied to the surface of the skin. The effectiveness of the UV light absorbers are tested on human subjects by testing a 1 cm square section of a subjects' back with predetermined amounts of lotion, exposing the treated areas to UV light for a period of time and thereafter making a visual comparison with untreated and fully masked skin areas. The SPF (skin protection factor) is calculated by comparing the effects of radiation on protected skin with the unprotected skin.

Besides the SPF determinations on humans, many in vitro methods and in vivo tests on animal models are also widely used. Some of these methods yield results which correlate well with SPF determined on humans and are useful tools for evaluating new compounds.

The following lotions and creams will serve to illustrate but not limit those which can be used in the practice of the invention.

In general, typical formulating techniques are well known to skilled formulators and usually require that the filtering agent be first added to the oil phase which is thereafter emulsified. With regards to examples 1-2 all ingredients can be mixed together and stirred in conventional apparatus. Since in many cases a single compound used at a reasonable concentration does not effectively protect throughout the whole region of the earth reaching solar UV spectrum, blends of two or more UV absorbers can be used in a formulation to afford greater protection. To illustrate the effectiveness of the compounds of the invention in sunscreen formulations Preparation 3 was formulated into creams and lotions for extensive testing. The formulations are shown in Table 1.

SUNSCREEN FORMULAS
TABLE 1

| Ingredient | Examples (% by Weight) | |
|---|---|---|
| | (1) | (2) |
| (A) | | |
| Compound of Prep. 3 | 5 | 2 |
| Mineral oil (Carnation) | 5 | 5 |
| Stearyl alcohol | .5 | .5 |
| Cetyl alcohol | .5 | .5 |
| Silicone oil (SF-96,350 cs) | .5 | .5 |
| Polyoxyethylene (21) stearyl ether | 2 | 2 |
| Polyoxyethylene (2) stearyl ether | 2 | 2 |
| (B) | | |
| Water (deionized) | 73.95 | 76.95 |
| Carbopol ® 934, (2% soln) | 10 | 10 |
| Sodium hydroxide (10% aq.) | .2 | .2 |
| (D) | | |
| DNDNH-55 (Glyco) | .35 | .35 |
| (E) | | |
| Dimethyl isosorbide | 0 | 0 |

BLENDING PROCEDURE FOR EXAMPLES 1 AND 2

Blend ingredients A and heat to 70° C. In a separate container heat ingredients B to 75° C. and add to A. Add C to AB then cool to 40° C. Add ingredient D with stirring.

In addition to their use in coating skin surfaces to prevent sunburn the compositions of the invention can also be employed in various formulations such as waxes, oils, lacquers and soft resins in the preparation of furniture and auto polishes, cosmetics, lipstick, hair treatments, skin formulations and contact lenses. The compounds of the invention act as filtering agents and maybe used singly or in combination to provide a wider range of protection. The following formulations are given to demonstrate a few of the many applications.

| Example No. | Filtering Agent | Carrier Ingredients | Composition (% by Wt) |
|---|---|---|---|
| 3 | Aerosol Hairdressing | Preparation 4 | 5.0 |
| | | Decaglycerol monolaurate | 2.0 |
| | | Polypropylene (200) monooleate | 3.0 |
| | | Ethoxylated (10) lanolin alcohols | 1.0 |
| | | Propylene glycol | 2.0 |
| | | Ethyl alcohol, anhydrous | 39.5 |
| | | Protein polypeptide (20% alcoholic) | 1.2 |
| | | Isopropyl myristate | 1.3 |
| | | Propellant 11 | 15.0 |
| | | Propellant 12 | 30.0 |
| | | Water | q.s. |

Procedure for Formula

Dissolve all ingredients in slightly warned ethylalcohol, avoiding loss of the alcohol, ad the water, and agitate well to disperse any haze. Filter the concentrate and fill into aerosol containers. Add propellants.

| Example No. | Filtering Agent | Carrier Ingredients | Composition (% by Wt) |
|---|---|---|---|
| 4 | Formula for Creamy Type Lipstick Base | | |
| | | Preparation 1 | 5 |
| | | Carnauba wax | 3 |
| | | Candelilla wax | 7 |
| | | Ozokerite ® | 3 |
| | | Beeswax | 7 |
| | | Lanolin | 10 |
| | | Castor oil | 60 |
| | | Isopropyl myristate | 5 |
| | | Perfume | q.s. |
| 5 | Water-In-Oil (W/O), Detergent Resistant, Liquid Auto Polish | | |
| | Part A | 2.00% Durmont 500 Montan Wax | (Dura Commodities) |
| | Part B | 0.75% DC 530 Silicone Fluid | (Dow Corning) |
| | | 4.25% DC 531 ® Silicone Fluid | |
| | | 1.50% SPAN ® 80 (ICI Americas) sorbitan monooleate | |
| | | 10.00% Kerosene | |
| | | 16.50% Stoddard Solvent | |
| | | 5.0% Preparation 2 | |
| | Part C | 10.00% Kaopolite ® SFO | (Kaopolite) |
| | Part D | 50.00% Water | |
| | Method of Preparation | | |
| | 1. Melt wax in Part A (85-90° C.) | | |
| | 2. Add Part B ingredients to melted wax and stir to blend well. Return temperature to 85-90° C. | | |
| | 3. Add Part C to Part A/Part B blend and mix until uniform with medium agitation. Keep temperature in the 85-90° C. range. | | |
| | 4. Heat Part D to 95° C. and slowly add to the blend with high speed stirring until emulsion is obtained. | | |
| | 5. Cool to 40-45° C. with continuous stirring. | | |
| | 6. Homogenize. | | |

| Example No. | Filtering Agent | Carrier Ingredients | Composition (% by Wt) |
|---|---|---|---|
| 6 | Neutral Base Lacquer | | |
| | Materials | | Pounds |
| | Urethane 60% N.V. | | 32 |
| | Long oil alkyd 60% N.V. | | 352 |
| | Triton X-45 | | 7.5 |
| | Nuxtra ® Calcium 6% | | 12 |
| | Bentone Jell 8% | | 28 |
| | Disperse the bentone jell under high speed cowles and add: | | |
| | Preparation 1 | | 16 |
| | Low odor mineral spirits | | 85 |
| | Cyclodex cobalt 6% | | 3 |
| | JK 270-70% | | 76 |
| | Water | | 205 |
| | Anti skin | | 2 |
| | Viscosity: 80–85 KU | | |
| | W/G: 7.84 | | |
| | 60° Gloss: 85 | | |
| | SAG: 6 ml | | |
| 7 | O/W Paraffin Wax Emulsion | | |
| | Part A | 50% Paraffin wax | |
| | | 5% SPAN 60/TWEEN 60 (50/50) (ICI Americas) (sorbitan monostearate/20 dendro sorbitan monostearate) | |
| | | 5% Preparation 2 | |
| | Part B | 40% Water | |
| | Method of Preparation | | |
| | 1. Melt Part A ingredients together and heat to 80° C. | | |
| | 2. Heat Part B to 85° C. | | |
| | 3. Add Part B to Part A slowly with moderate agitation until inversion occurs. Add remaining water rapidly. | | |
| | 4. Cool in cold water bath with slow agitation to approximately 35° C. | | |
| 8 | O/W Soft Microcrystalline Wax Emulsion | | |
| | Part A | 30% Microcrystalline wax (Ultraflex Amber Wax-Petrolite Corp.) | |
| | | 30% SPAN ® 60/TWEEN ® 60 (78/22) | |
| | | 5% Preparation 2 | |
| | Part B | 62% Water | |
| | Method of Preparation: | | |
| | 1. Melt together Part A ingredients and heat to 80–90° C. | | |
| | 2. Heat Part B to boiling. | | |
| | 3. Add Part B to Part A slowly with moderate agitation until inversion occurs. Add remaining water rapidly. | | |
| | 4. Remove from heat and cool to room temperature without stirring. | | |
| 9 | O/W Carnauba Wax Emulsion | | |
| | Part A | 10% Carnauba wax | |
| | | 3% TWEEN 80 (ICI Americas) (20 dendro sorbitan monooleate) | |
| | | 5% Preparation 3 | |
| | Part B | 82% Water | |
| | Method of Preparation: | | |
| | 1. Melt Part A ingredients together and heat to 95° C. and hold. | | |
| | 2. Heat Part B to boiling. | | |
| | 3. Add Part B to Part A slowly with moderately fast stirring until inversion occurs. Add remaining water rapidly. | | |
| | 4. Remove emulsion from heat and cool rapidly with stirring. | | |

SUNSCREEN LOTION

EXAMPLE 10

| PHASE | INGREDIENTS (SUPPLIERS) | PERCENT BY WEIGHT |
|---|---|---|
| A | Petrolatum, Snow White USP (Ruger) | 35.00 |
| | Brij ® 721 (ICI Americas surfactant) | 1.16 |
| | Brij 72 (ICI Americas surfactant) | 3.86 |
| | Silicone Oil, 350 cs (Ruger) | 3.00 |
| | Preparation 3 | 5.00 |
| | Uvinul M-40 (BASF) | 3.00 |
| B | Water | 48.08 |
| | Carbopol ® 934 (B. F. Goodrich) | 0.40 |
| C | Sodium Hydroxide (10% Aqueous Solution) | 0.40 |
| D | Dowicil ® 200 (DOW) | 0.10 |
| Preparation: | Heat (A) to 60° C. Heat (B) to 65° C. Add (B) to (A) slowly with moderate agitation. Add (C). Cool to 50° C. Add (D). Cool, while stirring to 35° C. | |

SUNSCREEN LOTION

EXAMPLE 11

| PHASE | INGREDIENTS (SUPPLIERS) | PERCENT BY WEIGHT |
|---|---|---|
| A | Arlamol ® E (ICI Americas, 30 dendro stearyl alcohol | 7.00 |
| | Stearyl Alcohol | 2.50 |
| | Silicone Oil, 350 cs (Ruger) | 5.00 |
| | Arlasolve 200 (ICI) | 2.10 |
| | Brij 72 (ICI) | 4.90 |
| | Preparation No 3 | 5.00 |
| | Preparation No 2 | 3.00 |
| B | Water | 70.00 |
| | Carbopol 934 (B. F. Goodrich) | 0.20 |
| C | Sodium Hydroxide (10% Aqueous Solution) | 0.20 |
| D | Dowicil 200 (DOW) | 0.10 |
| Preparation: | Heat (A) to 65° C. Heat (B) to 70° C. Add (B) to (A) slowly with moderate agitation. Add (C). Cool to 50° C. Add (D). Cool, | |

| PHASE | INGREDIENTS (SUPPLIERS) | PERCENT BY WEIGHT |
|---|---|---|
| | -continued | |
| | while stirring to 35° C. | |

SUNSCREEN LOTION
EXAMPLE 12

| PHASE | INGREDIENTS (SUPPLIERS) | PERCENT BY WEIGHT |
|---|---|---|
| A | Arlamol E (ICI) | 7.00 |
| | Stearyl Alcohol | 2.50 |
| | Silicone Oil, 350 cs (Rugher) | 5.00 |
| | Arlasolve ® 200 (ICI 20 dendro isohexadecyl alcohol) | 2.10 |
| | Brij 72 (ICI) | 4.90 |
| | Preparation 3 | 8.00 |
| B | Water | 70.00 |
| | Carbopol ® 934 (B. F. Goodrich) | 0.20 |
| C | Sodium Hydroxide (10% Aqueous Solution) | 0.20 |
| D | Dowicil 200 (DOW) | 0.10 |
| Preparation: | Heat (A) to 60° C. Heat (B) to 65° C. Add (B) to (A) slowly with moderate agitation. Add (C). Cool to 50° C. Add (D). Cool, while stirring to 35° C. | |

SUNSCREEN LOTION
EXAMPLE 13

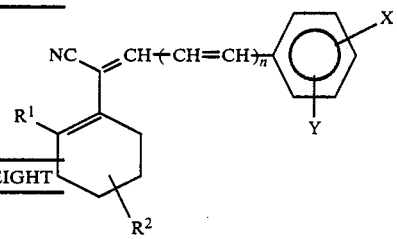

I

| PHASE | INGREDIENTS (SUPPLIERS) | PERCENT BY WEIGHT |
|---|---|---|
| A | Petrolatum, Snow White USP (Ruger) | 35.00 |
| | Brij 721 (ICI) | 1.16 |
| | Brij 72 (ICI) | 3.86 |
| | Preparation 3 | 8.00 |
| | Silicone Oil, 350 cs (Ruger) | 3.00 |
| B | Water | 49.08 |
| | Carbopol 934 (B. F. Goodrich) | 0.40 |
| C | Sodium Hydroxide (10% Aqueous Solution) | 0.40 |
| D | Dowicil 200 (DOW) | 0.10 |
| Preparation: | Heat (A) to 60° C. Heat (B) to 65° C. Add (B) to (A) slowly with moderate agitation. Add (C). Cool to 50° C. Add (D). Cool, while stirring to 35° C. | |

SUNSCREEN LOTION
EXAMPLE 14

| PHASE | INGREDIENTS (SUPPLIERS) | PERCENT BY WEIGHT |
|---|---|---|
| A | Arlamol E (ICI) | 7.00 |
| | Stearyl Alcohol | 2.50 |
| | Silicone Oil, 350 cs (Ruger) | 5.00 |
| | Arlasolve ® 200 (ICI) | 2.10 |
| | Brij 72 (ICI) | 4.90 |
| | Preparation 1 | 5.50 |
| B | Water | 72.50 |
| | Carbopol 934 (B. F. Goodrich) | 0.20 |
| C | Sodium Hydroxide (10% Aqueous Solution) | 0.20 |
| D | Dowicil 200 (DOW) | 0.10 |
| Preparation: | Heat (A) to 65° C. Heat (B) to 70° C. Add (B) to (A) slowly with moderate agitation. Add (C). Cool to 50° C. Add (D). Cool, while stirring to 35° C. | |

What is claimed is:
1. A compound of the formula:

wherein n is 0 or 1, but when n is 0, $R^1$ is H, an alkyl group having from 1 to 10 carbon atoms, $R^2$ is H, an alkyl group having from 1 to 10 carbon atoms, $-OR^3$, $-NHR^3$, $-N(R^3)_1$ and $-CO_2R^4$ where $R^3$ is an alkyl group having from 1 to 10 carbon atoms and X and Y are independently selected from the group consisting of H, alkyls of from 1 to 10 carbon atoms halogen, $-CN$, $-NO_2$, $-NHR^4$, $-N(R^4)_2$ $-OR^4$, and $-CO_2R^4$ where $R^4$ is an alkyl group having from 1 to 10 carbon atoms and when n is 1, $R^1$ and $R^2$ are as described above and X and Y are hydrogen.

2. A compound of claim 1 wherein n is 0 and $R^2$, $R^3$, X and Y are hydrogen.

3. A compound of claim 1 wherein n is 1 and $R^1$, $R^2$, X and Y are hydrogen.

4. A compound of claim 1 wherein n is 0, $R^1$, $R^2$ and X are hydrogen and Y is 4-methoxy.

5. A compound of claim 1 wherein n is 1, $R^1$ is hydrogen, $R^2$ is 4-t-butyl and X and Y are hydrogen.

* * * * *